United States Patent

Byrnes et al.

[11] Patent Number: 5,263,945
[45] Date of Patent: Nov. 23, 1993

[54] FEMALE LUER FITTING WITH SPIRALLY SPACED INTERIOR LOCKING PROTUBERANCES

[75] Inventors: Raymond A. Byrnes; Robert A. DiPetrillo, both of Providence, R.I.

[73] Assignee: Contech Packaging, Inc., Providence, R.I.

[21] Appl. No.: 750,632

[22] Filed: Aug. 27, 1991

[51] Int. Cl.⁵ ............................................. A61M 25/00
[52] U.S. Cl. .................................. 604/283; 604/905; 604/240; 285/238
[58] Field of Search ......................... 604/283, 240–243, 604/905, 280, 275; 285/238

[56] References Cited

U.S. PATENT DOCUMENTS

| | | | |
|---|---|---|---|
| 2,103,838 | 12/1937 | Bach | 285/238 |
| 3,472,457 | 10/1969 | McAvoy | 285/238 X |
| 3,491,757 | 1/1970 | Arce | 604/242 |
| 3,542,024 | 11/1970 | Burke | 604/241 |
| 3,977,403 | 8/1976 | Patel | 604/243 |
| 4,040,421 | 8/1977 | Young | 604/243 X |
| 4,369,781 | 1/1983 | Gilson et al. | 604/403 |
| 4,430,079 | 2/1984 | Thill et al. | 604/154 |
| 4,430,080 | 2/1984 | Pasquini et al. | 604/240 |
| 4,439,188 | 3/1984 | Dennehey et al. | 604/283 |
| 4,816,020 | 3/1989 | Brownell | 604/97 |
| 5,147,336 | 9/1992 | Wendell et al. | 604/283 |

FOREIGN PATENT DOCUMENTS

| | | | |
|---|---|---|---|
| 248979 | 12/1987 | European Pat. Off. | 604/243 |
| 3631812 | 3/1987 | Fed. Rep. of Germany | 285/238 |
| 751433 | 9/1933 | France | 604/243 |
| 1125688 | 11/1956 | France | 604/283 |
| 418857 | 11/1934 | United Kingdom | 285/238 |
| 721672 | 1/1955 | United Kingdom | 285/238 |

Primary Examiner—C. Fred Rosenbaum
Assistant Examiner—Mark O. Polutta

[57] ABSTRACT

A female fitting for a Luer which comprises a hollow, cylindrical member having means to attach it to the Luer at one end thereof, and means for quickly and manually attaching a plastic tubing to the opposite end of the member. In order to attach the tubing, the interior surface of the fitting adjacent this end is provided with protuberances on the inside surface thereof which engage with the tubing as the tubing is thrust thereinto in order to provide a substantially mechanical lock by being impressed into the material of the tubing. The material of the tubing is softer and more impressionable than the material of the fitting itself and its protuberances. The protuberances are arranged in spaced relation on a spiral path.

9 Claims, 1 Drawing Sheet

FEMALE LUER FITTING WITH SPIRALLY SPACED INTERIOR LOCKING PROTUBERANCES

FIELD OF THE INVENTION

The field of the invention is medical and it relates to a female fitting for a Luer which is used to hold the usual plastic tubing in position while the Luer is being used.

BACKGROUND OF THE INVENTION

The Luer is a well known device used especially for blood transfusions but also for other medical procedures with respect to patients in transference of the fluid. The female fitting which is the subject of the present invention was originally made of steel and stainless steel and of course re-sterilized after every use. In recent times, these Luers in concert with other hospital and medical devices, are especially made to be used once and then disposed of, and the female fitting aforesaid was made of plastic material at much less cost. The trouble with this plastic fitting is that it is often not well secured with reference to the plastic tubing that leads from it to the patient and on occasion it accidently becomes detached, depositing whatever material is in the Luer onto the hospital bed or the floor etc., and the procedure has to be done over again. It is the object of this invention, to make at very small expense, a female Luer fitting which will lend itself to be well seamed to the male end of the plastic hose to cause an at least partial, mechanical connection preventing separation under accidental circumstances to a far greater degree when using the conventional and widely known plastic tubing for the purpose of transferring fluid, thus resulting in an inexpensive fitting that can be disposed of whenever desirable.

SUMMARY OF THE INVENTION

The Luer female fitting of the present invention is injection molded of suitable material and it has a passageway through it to lead from one end adjacent the Luer to the other end which accepts the proximate end of the plastic tube so that the operation may be continued until the Luer is exhausted. In the present case, the female fitting which accepts the male end of the plastic tube is provided with a plurality of protrusions of very small size which extend into the interior of the female fitting and which impinge upon and actually displace to a small degree the material of which the tubing is made. The protuberances are arranged at different distances from the end of the fitting inwardly and at preferably 120 degrees apart on the interior circumference of the female fitting. Thus when the plain ended proximate end of the tubing is thrust into the female fitting at the opposite end thereof from the Luer, this action tends to score the outside surface of the tubing forming a semi or even a complete thread, and the protuberances are located on a spiral which inherently is provided by the operator when thrusting the end of the tubing into the female fitting. The operator turns the tube in a clockwise direction at least partially imbedding the protuberances into the material of the tubing and thereby forms a substantially mechanical lock between the tubing and the Luer fitting.

PREFERRED EMBODIMENT OF THE INVENTION

In order to provide an inexpensive fitting, which will operate in an improved manner over the prior art, substantially the same fitting is used as always. This fitting has one end which is fastened to the Luer by any secured means such as threads and being a short fitting, hollow from end to end and which receives at its end remote from the Luer a conventional plastic pipe or tubing which is applied thereto by a twisting motion. The end of the fitting which receives the tube is provided with a plurality of interior protuberances arranged at differing distances from the entrance thereinto and at 120 degrees circumferentially apart so that as the proximate end of the tubing is utilized as a male member and is thrust into the hollow female fitting it is given a clockwise twist so that the protuberances impinge one after another upon the outside diameter of the tubing. This provides a mechanical locking device because the tubing is displaced in part whenever it encounters one of the protuberances and continued thrust and twist motion just about locks the end of the plastic tubing to the fitting by digging into the outside diameter of the same by means of the protuberances in a helical fashion. Thus the general effect of the screw thread is obtained but no screw threads have to be injection molded for either the fitting or the end of the tubing.

Figure 1:
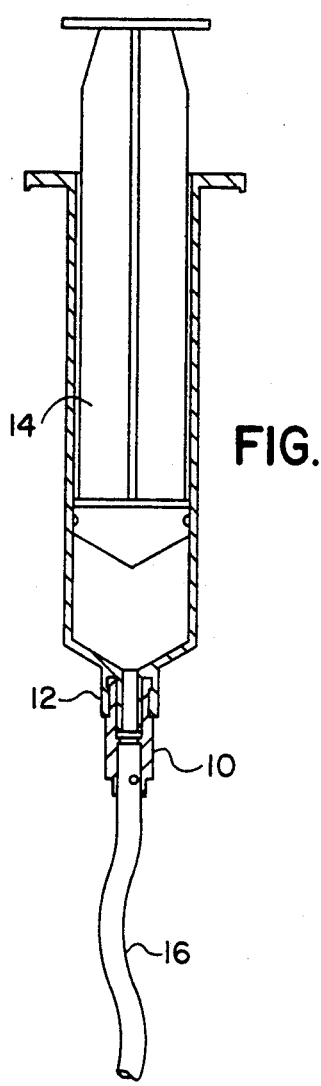
FIG. 1 is a longitudinal sectional view of the environment of a female luer fitting.

The novel female Luer fitting is indicated generally at 10 in FIG. 1, connected as it is to the outlet of the Luer 12 and the tubing connected to the fitting is illustrated at 16. It is emphasized that the invention in this case is not in the end of the fitting attached to Luer 12 but in the opposite end thereto to which the tubing 16 is manually attached, which will be explained later. Also, the fitting 10 is of harder plastic material than is the tubing itself.

Figure 2:
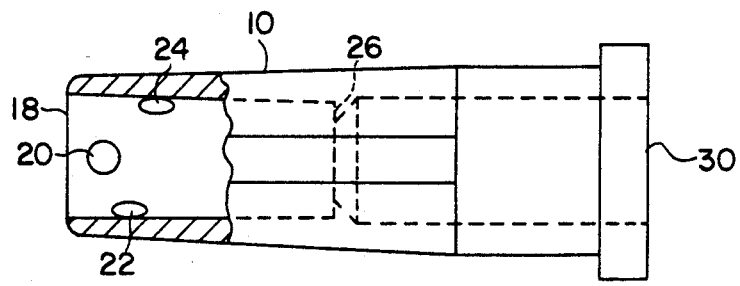
FIG. 2 is a longitudinal elevational view, part in section, of the fitting.
Figure 3:
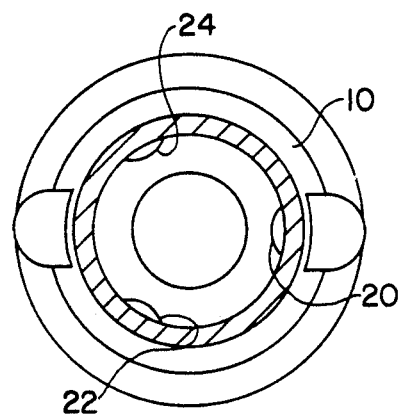
FIG. 3 is an end view of the fitting looking in the direction of the arrow A in FIG. 4.

The fitting 10 per se has an entrance end 18 for the tubing, see FIG. 2. The tube will fit into and will become strongly but only temporarily attached to the fitting 10 and the opposite end of the fitting at 30 may be provided with some kind of connection to the outlet of the Luer 12 but this is not of importance to the present invention.

The entrance end 18 of the Luer fitting 10 for receiving the tubing 16 is provided with means for a mechanical or semi-mechanical lock for the proximate end 31 of the tubing, and this resides in a number of protuberances on the inside diameter of the fitting 10 as at 20, 22 and 24. These protuberances are all alike and are injection molded at the time of molding of the fitting 10, all in one piece. There may also be a ring barrier 26 located midway of the inside diameter of the hollow fitting to locate the proximate end of the tubing as will be clear. Also the exit end of the exit of the Luer itself is stopped by the barrier so that it will be seen first that the fitting is attached to the Luer exit tip and then the proximate end 31 of the tubing is attached to the opposite end of the fitting at 18.

Figure 4:
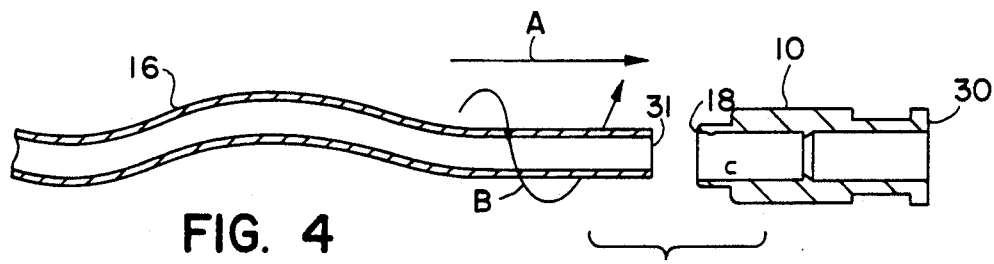
FIG. 4 is a diagram illustrating the act of connecting the tubing to the fitting.
Figure 5:
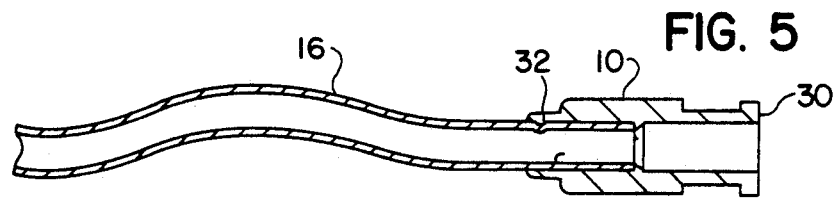
FIG. 5 is a longitudinal sectional view illustrating the fitting in position with respect to the tubing.

The three (or 2 or more than 3) protuberances are permeably all alike and when the proximate end 31 of the tubing 16 is taken in one hand and is thrust into the entrance end 18 of the fitting 10, see FIG. 4, it is given a right hand twist manually as indicated by arrow B so that the leading end of the tubing as indicated at 31, FIG. 4, first encounters protuberance 20 which will tend to displace slightly a groove at the outside diameter of the material forming the tubing, and the proximate end of the tubing will then encounter the second protuberance 22 and turning as illustrated by arrow B in FIG. 4 the second protuberance, as well as the first protuberance, tends to form a very slight groove in the proximate end of the outside surface of the tubing. Further pushing in and turning of the tubing will cause the same action with respect to the third protuberance 24 so that when finally seated, the proximate end of the tubing will have been scored or indented slightly in a spiral form with respect to the softer material of the tubing. A substantial lock is made between the harder material of the fitting itself, and the softer material of the tubing, as at 32. Whereas it is possible to manually disengage the parts, it is very unlikely that any accidental separation will occur.

The three protuberances shown are located at 120 degrees apart as arranged about the inside diameter of the fitting, and if 4 protuberances were to be used, they would be located at 90 degrees apart for the same purpose.

It has been found that although the invention is not limited to the number of protuberances shown, i.e. 3, this is probably the best design for the present invention as only two protuberances would be a too light engagement between tube and fitting, and four protuberances are really not necessary. The angular distance between the centers of the protuberances is determined by dividing 360° by N where N equals the number of protuberances. When N equals 4, the angular distance is 90°; when N equals 2, the angular distance equals 180°. As previously indicated, it is preferred that N equal 3, therefore the angular distance between the centers of the protuberances will be 120°.

We claim:

1. A female Luer fitting comprising an elongated hollow body member having open opposite ends and a through passage therein between said open ends,
   said hollow body having adjacent one end a smooth interior circumferential surface forming an elongated socket for the reception of the proximate end of a cylindrical plastic tube,
   a plurality of small protuberances located at different distances from said one end of said hollow body on said interior circumferential surface along a helical path spiralling inwardly from said one end and integral with said hollow body member,
   said protuberances being of substantially similar size and shape each with a generally spherical surface contour, and being serially spaced at substantially equal distances along said helical path, the angular spacing between protuberances being substantially equal to 360° divided by the number of said protuberances,
   means at the other end of said hollow body for securing said hollow body to a Luer outlet.

2. The female Luer fitting of claim 1 wherein the number of said protuberances is within the range of from two to four.

3. The female Luer fitting of claim 2 wherein the number of said protuberances is three and the angular spacing between protuberances is substantially 120°.

4. The female Luer fitting of claim 2 wherein the number of said protuberances is four and the angular spacing between said protuberances is substantially 90°.

5. The female Luer fitting of claim 1 wherein said hollow body and said protuberances are injection molded.

6. The female Luer fitting of claim 1 wherein said hollow body and integral protuberances are of a hard plastic material.

7. The female Luer fitting of claim 1 wherein said hollow body member has a ring barrier within said through passage intermediate said opposite ends to provide as abutment stop for a cylindrical plastic tube inserted into said socket.

8. In combination a female Luer fitting and a cylindrical plastic tube coupled thereto,
   said female Luer fitting comprising an elongated hollow body member having open opposite ends and a through passage therein between said open ends,
   said hollow body having adjacent one end a smooth interior circumferential surface forming an elongated socket for the reception of the proximate end of a cylindrical plastic tube,
   a plurality of small protuberances located at different distances from said one end of said hollow body on said interior circumferential surface along a helical path spiralling inwardly from said one end and integral with said hollow body member,
   said protuberances being of substantially similar size and shape each with a generally spherical surface contour, and being serially spaced at substantially equal distances along said helical path, the angular spacing between protuberances being substantially equal to 360° divided by the number of said protuberances,
   means at the other end of said hollow body for securing said hollow body to a Luer outlet,
   said hollow body member and protuberances being of a hard material compared to the plastic material of said cylindrical tube which is relatively soft,
   said cylindrical plastic tube being inserted into said socket at said one end of said hollow body member with a twisting motion,
   the exterior surface of said cylindrical plastic tube being inwardly deformed along a helical path by the protuberances on the interior surface of said socket to provide a mechanical lock between said cylindrical plastic tube and said female Luer fitting.

9. The combination of claim 7 wherein said hollow body member has a ring barrier within said through passage intermediate said opposite ends providing an abutment stop for the proximate end of said cylindrical plastic tube.

* * * * *